United States Patent [19]

Koehler et al.

[11] Patent Number: 5,672,781

[45] Date of Patent: Sep. 30, 1997

[54] PROCESS FOR THE PRODUCTION OF FATTY ALCOHOLS BASED ON VEGETABLE FATS AND OILS BY FRACTIONATION

[75] Inventors: Michael Koehler; Karl-Heinz Schmid, both of Mettmann; Guenther Demmering, Solingen; Horst-Dieter Komp, Langenfeld; Hans-Peter Kubersky, Solingen, all of Germany

[73] Assignee: Henkel Kommanditgesellschaft auf Aktien, Duesseldorf, Germany

[21] Appl. No.: 633,733

[22] PCT Filed: Oct. 12, 1994

[86] PCT No.: PCT/EP94/03348

§ 371 Date: May 9, 1996

§ 102(e) Date: May 9, 1996

[87] PCT Pub. No.: WO95/11210

PCT Pub. Date: Apr. 27, 1995

[30] Foreign Application Priority Data

Oct. 20, 1993 [DE] Germany ............ 43 35 781.4

[51] Int. Cl.⁶ .......................... C07C 29/80; C07C 31/125
[52] U.S. Cl. .................................................. 568/885
[58] Field of Search .......................................... 568/885

[56] References Cited

U.S. PATENT DOCUMENTS 2,004,131  6/1935  Reid .......................... 260/156
5,043,485  8/1991  Fleckenstein et al. ............. 568/885
5,138,106  8/1992  Wilmott et al. .................. 568/885

OTHER PUBLICATIONS

Seifen–Öle–Fette–Wasche 109, 225 (1983).
Ullmann's Enzyclopaedie der technischen Chemie, Verlag Chemie, Weinheim, 4th Edition, vol. 11, p. 436 et seq. (1976).
Römpp Chemie Lexikon, Thieme Verlag, Stuttgart, 9th Edition, vol. 3, p. 2305 (1990).
Katt, et al, "Indian Journal of Technology" (1967), vol. 5, No. 5, pp. 155–157, Reprint.

Primary Examiner—C. Warren Ivy
Assistant Examiner—Lyman H. Smith
Attorney, Agent, or Firm—Ernest G. Szoke; Wayne C. Jaeschke; John E. Drach

[57] ABSTRACT

Fatty alcohols of the formula I $$R^1OH \qquad (I)$$

wherein $R^1$ is a saturated or unsaturated, linear or branched aliphatic radical having from about 8 to about 22 carbon atoms are made by an improvement in the process which comprises hydrogenating a fatty acid, a fatty acid methyl ester or a combination thereof to form a fatty alcohol. The improvement comprises removing a head fraction from the fatty acid, the fatty acid methyl ester or the fatty alcohol in such a quantity that the fatty alcohol has an iodine value of from about 20 to about 110 and less than about 4.5% by weight of conjugated compounds.

2 Claims, No Drawings

PROCESS FOR THE PRODUCTION OF FATTY ALCOHOLS BASED ON VEGETABLE FATS AND OILS BY FRACTIONATION

This application is a 35 U.S.C. 371 National Stage filing of PCT/EP94/03348 published as WO95/11210 on Apr. 27, 1995.

BACKGROUND OF THE INVENTION

This invention relates to a process fort the production of fatty alcohols based on vegetable fats and oils with an iodine value in the range from 20 to 110, to fatty alcohols based on vegetable fats and oils with an iodine value of 20 to less than 95 and to the use of these products for the production surface-active formulations.

STATEMENT OF RELATED ART

Fatty compounds, particularly unsaturated fatty alcohols, are important intermediates for a large number of products of the chemical industry, for example for the production of surfactants and skin-care products. An overview of these intermediate products is provided, for example, by U. Ploog et al. in Seifen-öle-Fette-Wachse 109, 225 (1983). They are produced from more or less unsaturated fatty acid methyl esters which may be hydrogenated, for example, in the presence of chromium- or zinc-containing mixed catalysts [Ullmann's Enzyclopaedie der technischen Chemie, Verlag Chemie, Weinheim, 4th Edition, Vol. 11, pages 436 et seq.].

The prior art in this field is an industrial process using animal fats and oils which has also been carried out by applicants and in which the unsaturated fatty alcohols accumulating after hydrogenation are distilled at a bottom temperature of, for example, 220° to 250° C. and under a reduced pressure of 1 to 20 mbar, as measured at the head of the column. Since the production of unsaturated fatty alcohols involves high costs, the distillation conditions were designed to minimize the loss of raw materials. In fact, a yield of around 90% of the theoretical (and hence a loss of 10%) was achieved in this way. Unfortunately, the products had a distinct odor. Another disadvantage was that the fatty alcohols of the prior art show unsatisfactory storage and low-temperature behavior.

Unsaturated fatty alcohols with iodine values of 20 to 95 are particularly preferred for applicational reasons because they have a particularly favorable solidification point for use in cosmetic products. Hitherto, unsaturated fatty alcohols with iodine values in the range mentioned have always been based on animal fats. The desired iodine value range is established by blending various products with different iodine value ranges. The iodine value range cannot be established by distillation-based processes because the iodine value or rather the iodine value range of fatty alcohols or fatty acids based on animal fats remains substantially constant during fractionation.

However, animal fats have the disadvantage that they are extremely heterogeneous. For example, animal fats contain nitrogen-containing compounds, such as amides or steroids, such as cholesterol for example, which are directly or indirectly responsible for the unpleasant odor of the products mentioned above. The nitrogen-containing compounds can enter into secondary reactions which adversely affects product stability, particularly oxidation stability, and leads to discolored products.

There is an urgent need in the cosmetic market in particular for purer raw materials of higher quality—a requirement which normally can only be satisfied by increasingly more expensive technical processes and additional purification steps. In the case of unsaturated fatty alcohols, there is a need above all for products with improved color and odor quality and more favorable low-temperature behavior. Added to this is the fact that, in recent years, consumer behavior has changed to the extent that consumers now attribute considerable importance to purely vegetable products.

Known vegetable fatty alcohols have iodine values below 20 or very high iodine values above 100. Fatty alcohols with iodine values in the applicationally preferred range of 20 to 95 mentioned above are not known. The blending of fatty alcohols with very different iodine values does not lead to satisfactory products.

The problem addressed by the present invention was to provide fatty alcohols based on vegetable fats and oils which would have iodine values in the applicationally preferred range and which, at the same time, would have greater oxidation stability than unsaturated fatty alcohols based on animal fats and equivalent or better low-temperature behavior.

DESCRIPTION OF THE INVENTION

The present invention relates to a process for the production of fatty alcohols based on vegetable fats and oils with an iodine value in the range from 20 to 110 which contain substantially unsaturated fatty alcohols and mixtures of saturated and unsaturated fatty alcohols corresponding to general formula (I):

$$R^1OH \qquad (I)$$

where $R^1$ is a saturated or unsaturated, linear or branched alkyl group containing 8 to 22 carbon atoms, in which the triglycerides present in the vegetable fats and oils as raw materials a) are hydrolyzed to the fatty acids by pressure hydrolysis and then optionally esterified with methanol or b) are transesterified to the fatty acid methyl esters and c) the fatty acid or the fatty acid methyl ester is hydrogenated to the fatty alcohol, characterized in that the fatty acid, the fatty acid methyl ester and/or the hydrogenation product are fractionated by removing a head fraction in such a quantity that the end product has an iodine value of 20 to 110.

Surprisingly, it has been found that, in contrast to products based on animal fats, it is possible to produce fatty alcohols based on vegetable fats and oils with iodine values in the range mentioned above which contain substantially unsaturated fatty alcohols and mixtures of saturated and unsaturated fatty alcohols corresponding to general formula (I), the iodine value being adjustable to the desired range by simple fractionation in accordance with applicational requirements. The products based on vegetable fats and oils obtained by the process according to the invention show better oxidation stability and less odor than corresponding products based on animal fats.

The present invention also relates to fatty alcohols based on vegetable fats and oils with an iodine value of 20 to less than 95 which contain substantially unsaturated fatty alcohols and mixtures of saturated and unsaturated fatty alcohols corresponding to general formula (I):

$$R^1OH \qquad (I)$$

in which $R^1$ is a saturated or unsaturated, linear or branched alkyl group containing 8 to 22 carbon atoms. The fatty alcohols according to the invention based on vegetable fats and oils have an iodine value of 40 to 85. In addition, compounds corresponding to formula (I), in which $R^1$ is an alkyl group containing 12 to 20 carbon atoms, are preferred.

The fatty alcohols according to the invention show particularly high stability when only a low percentage of conjugated compounds is present. The fatty alcohols according to the invention based on vegetable fats and oils preferably have a content of conjugated compounds below 6% by weight and, more preferably, below 4.5% by weight.

Unsaturated or partly unsaturated vegetable fats and oils are used as starting materials for the process according to the invention. Palm oil, palm stearin oil, palm kernel olein oil, coconut oil, palm kernel oil, sunflower oil, new rapeseed oil, soybean oil, peanut oil, rapeseed oil, linseed oil and olive oil are particularly preferred. The fats consisting essentially of triglycerides are converted into the fatty acids in known manner by pressure hydrolysis and optionally esterified with methanol or are transesterified with methanol to the fatty acid methyl ester. The fatty acid or the fatty acid methyl ester is then hydrogenated to the corresponding fatty alcohol by known methods. The percentage content of saturated and unsaturated constituents and the chain length distribution are determined by the vegetable oils used. In the above compounds corresponding to formula (I), $R^1$ is an alkyl radical containing 8 to 22 carbon atoms and preferably 12 to 20 carbon atoms.

Through the use of vegetable fats and oils as starting products, the fatty acids/fatty acid methyl esters used or the hydrogenation product are mixtures of fatty acids, fatty acid methyl esters or fatty alcohols differing in their chain lengths. According to the invention, the iodine value of the fatty alcohols to be produced is adjusted by fractionating the fatty acids obtained by pressure hydrolysis, the fatty acid methyl esters obtained by transesterification of the triglycerides or the hydrogenation product obtained by hydrogenation of the fatty acid or the fatty acid methyl ester. The iodine value of the product to be fractionated is determined before fractionation. Depending on the starting product or its iodine value and the desired iodine value, a certain quantity of head fraction is removed during fractionation. By removing the head fraction, the iodine value of the fatty alcohol is increased. To adjust the iodine value of the product, the iodine value of the product which has not yet distilled over is monitored during fractionation. For example, it is possible by the process according to the invention to obtain from coconut oil/palm kernel oil a fatty acid or fatty acid methyl ester fraction which contains fatty acid or fatty acid methyl ester with chain lengths of 16 to 18 carbon atoms, so-called $C_{16/18}$ fatty acid or fatty acid methyl ester, as its principal constituent. The required chain length distribution can also be adjusted by corresponding fractionation of the fatty alcohol.

The fractionation conditions under reduced pressure for the unsaturated fatty alcohols obtained, for example, from the hydrogenation stage have long been known. Fractionation may be carried out in batches or continuously under reduced pressure. Superheated steam, for example, may be used for heating, the bottom temperature being in the range from 220° to 250° C. for example.

The actual fractionation process takes place in a packed column with fittings characterized by a low pressure loss. Suitable fittings are, for example, ordered metal packs. Further examples can be found in RÖMPP Chemie Lexikon, Thieme Verlag, Stuttgart, 9th Edition, Vol. 3, page 2305 (1990) under the keyword "column fittings" and in the literature cited therein.

The necessary fine vacuum of 1 to 20 mbar at the head of the column can be obtained, for example, with water ring pumps and preceding steam jet pumps. The pressure drop throughout the distillation plant should preferably be no more than 20 mbar.

An improvement in the end product can be obtained by distilling the unsaturated fatty alcohols in such a way that a residue of up to 10% by weight and preferably from 2 to 7% by weight is obtained. The color value and odor of the end products are distinctly further improved by this measure.

Industrial Applications

The unsaturated fatty alcohols based on vegetable fats and oils obtainable by the process according to the invention are substantially colorless and odorless and show particularly favorable low-temperature behavior. Accordingly, they are suitable as raw materials for the production of laundry detergents, dishwashing detergents and cleaning products and also hair-care and body-care products, in which they may be present in quantities of 1 to 50% by weight and preferably 5 to 30% by weight, based on the particular product.

The invention is illustrated by the following Examples:

EXAMPLES

Fatty acid methyl esters were hydrogenated in a typical hydrogenation reactor under a pressure of around 225 bar and at a temperature of 275° to 330° C. in the presence of a $CuCrO_4$ catalyst. The hydrogenation product is distilled, a corresponding head fraction being removed.

Example 1

A $C_{12/18}$ palm kernel oil methyl ester obtained from the transesterification of palm kernel oil and subsequent fractionation was fractionated to a $C_{12/14}$ and $C_{16/18}$ methyl ester. The $C_{16/18}$ methyl ester was hydrogenated to the fatty alcohol as described above. The crude product was distilled in a two-stage vacuum fractionating unit, a head fraction of 3% by weight being removed and a residue of 3% by weight remaining.

A fatty alcohol (FA) with the following chain distribution and the following characteristic data was obtained:

| | |
|---|---|
| FA C 12 | 0.2% by weight |
| FA C 14 | 4.5% by weight |
| FA C 15 | 0.3% by weight |
| FA C 16 | 25.1% by weight |
| FA C 16 ' | 0.4% by weight |
| FA C 17 | 0.3% by weight |
| FA C 18 | 8.9% by weight |
| FA C 18 ' | 52.5% by weight |
| FA C 18 '' | 2.9% by weight |
| FA C 18 '' conj. | 3.2% by weight |
| FA C 18 ''' | 0.1% by weight |
| FA C 20 | 0.6% by weight |
| Acid value | = 0.02 |
| Saponification value | = 0.35 |
| OH value | = 213.5 |
| Iodine value | = 61.3 |
| $H_2O$ content | = 0.02 |
| Softening point | = 26.6° C. |
| Hydrocarbon content | = 0.87% by weight |
| CO value | = 360 |
| Hazen | = <10 |

Example 2

The product obtained from the hydrogenation in Example 1 is distilled in such a way that a head fraction of around 18% by weight is removed, a fatty alcohol with a relatively high iodine value of 75 being obtained.

This fatty alcohol has the following chain distribution and the following characteristic data:

| FA C 12 | 0.0% by weight |
|---|---|
| FA C 14 | 0.1% by weight |
| FA C 15 | 0.1% by weight |
| FA C 16 | 12.1% by weight |
| FA C 16 ' | 0.2% by weight |
| FA C 17 | 0.3% by weight |
| FA C 18 | 11.5% by weight |
| FA C 18 ' | 66.5% by weight |
| FA C 18 '' | 3.7% by weight |
| FA C 18 '' conj. | 4.3% by weight |
| FA C 18 ''' | 0.2% by weight |
| FA C 20 | 0.4% by weight |
| Acid value | = 0.02 |
| Saponification value | = 0.40 |
| OH value | = 210.5 |
| Iodine value | = 75 |
| H$_2$O content | = 0.02 |
| Softening point | = 23.2° C. |
| Hydrocarbon content | = 0.13% by weight |
| CO value | = 306 |
| Hazen | = 5 |

Example 3

Starting out from a mixture of a C$_{16/18}$ palm kernel oil methyl ester (70% by weight) and rapeseed oil methyl ester (30% by weight) prepared from new rapeseed oil, a fatty alcohol with the following chain distribution and the following characteristic data was prepared as described in Example 1:

| FA C 12 | 0.0% by weight |
|---|---|
| FA C 14 | 0.0% by weight |
| FA C 15 | 0.2% by weight |
| FA C 16 | 23.1% by weight |
| FA C 16 ' | 0.8% by weight |
| FA C 17 | 0.4% by weight |
| FA C 18 | 6.4% by weight |
| FA C 18 ' | 60.3% by weight |
| FA C 18 '' | 4.6% by weight |
| FA C 18 '' conj. | 3.2% by weight |
| FA C 18 ''' | 0.1% by weight |
| FA C 20 | 0.6% by weight |
| Acid value | = 0.02 |
| Saponification value | = 0.35 |
| OH value | = 213 |
| Iodine value | = 73.9 |
| H$_2$O content | = 0.03 |
| Softening point | = 22.9° C. |
| Hydrocarbon content | = 0.2% by weight |
| CO value | = 279 |
| Hazen | = <10 |

What is claimed is:

1. An improved process for making a fatty alcohol of the formula I $$R^1OH \qquad (I)$$

wherein $R^1$ is a saturated or unsaturated, linear or branched aliphatic radical having from about 8 to about 22 carbon atoms which comprises hydrogenating a fatty acid, a fatty acid methyl ester or a combination thereof to form a fatty alcohol wherein the improvement comprises removing a head fraction from said fatty acid, said fatty acid methyl ester or said fatty alcohol in such a quantity that said fatty alcohol has an iodine value of from about 20 to about 110 and less than about 4.5% by weight of conjugated compounds.

2. A fatty alcohol of the formula I $$R^1OH \qquad (I)$$

wherein $R^1$ is a saturated or unsaturated, linear or branched aliphatic radical having from about 8 to about 22 carbon atoms made by an improved process which comprises hydrogenating a fatty acid, a fatty acid methyl ester or a combination thereof to form a fatty alcohol wherein the improvement comprises removing a head fraction from said fatty acid, said fatty acid methyl ester or said fatty alcohol in such a quantity that said fatty alcohol has an iodine value of from about 20 to about 110 and less than about 4.5% by weight of conjugated compounds.

* * * * *